United States Patent [19]

Miesel

[11] 4,338,321

[45] Jul. 6, 1982

[54] FORMULATIONS OF DIHALOBENZOYL-SUBSTITUTED-PYRIDINYLUREA INSECTICIDES

[75] Inventor: John L. Miesel, Indianapolis, Ind.

[73] Assignee: Eli Lilly and Company, Indianapolis, Ind.

[21] Appl. No.: 233,429

[22] Filed: Feb. 11, 1981

Related U.S. Application Data

[60] Division of Ser. No. 114,770, Jan. 23, 1980, Pat. No. 4,281,003, which is a continuation-in-part of Ser. No. 938,723, Aug. 31, 1978, Pat. No. 4,219,557.

[51] Int. Cl.³ .................... C07D 213/75; A01N 43/40
[52] U.S. Cl. ...................................... 424/263; 546/306
[58] Field of Search .......................... 424/263; 546/306

[56] References Cited

U.S. PATENT DOCUMENTS

| | | | |
|---|---|---|---|
| 4,173,639 | 8/1978 | Suhr | 424/263 |
| 4,218,870 | 7/1980 | Gibbs | 424/263 |
| 4,219,557 | 8/1980 | Miesel | 424/263 |
| 4,264,605 | 6/1979 | Suhr et al. | 424/263 |

FOREIGN PATENT DOCUMENTS 2848794  5/1980  Fed. Rep. of Germany ...... 546/306

OTHER PUBLICATIONS

De Milo et al., Journal of Agriculture & Food Chemistry, vol. 26, pp. 164–166, (1978).

Deady, Synthetic Communications, vol. 7, pp. 509, (1977).

*Primary Examiner*—Alan L. Rotman
*Attorney, Agent, or Firm*—Joseph A. Jones; Arthur R. Whale

[57] ABSTRACT

2,6-Dihalobenzoyl 5-substituted-2-pyridinyl ureas are potent insecticides. A method of reducing a population of manure-breeding insects is also provided.

9 Claims, No Drawings

FORMULATIONS OF DIHALOBENZOYL-SUBSTITUTED-PYRIDINYLUREA INSECTICIDES

CROSS-REFERENCE

This application is a division of co-pending application Ser. No. 114,770, filed Jan. 23, 1980, now U.S. Pat. No. 4,281,003, which was a continuation-in-part of co-pending application Ser. No. 938,723, filed Aug. 31, 1978, now U.S. Pat. No. 4,219,557.

BACKGROUND

Field of the Invention

This invention provides novel 1-(2,6-dihalobenzoyl)-3-(5-substituted-2-pyridinyl)urea insecticides, and insecticidal methods using the novel compounds and some related compounds for the control of manure-breeding insects.

SUMMARY OF THE INVENTION

This invention provides novel insecticides of the formula

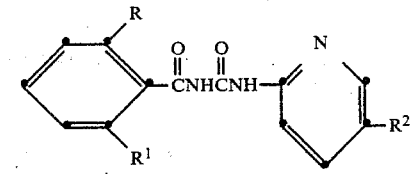

wherein
R and $R^1$ are fluoro, and
$R^2$ is trifluoromethyl;
or wherein R is chloro, $R^1$ is fluoro, and $R^2$ is chloro, bromo or trifluoromethyl;
or an acid addition salt thereof.

Insecticidal methods and compositions are also provided.

The invention also provides a method of reducing a population of manure-breeding insects which comprises orally administering to a warm-blooded animal an insecticidally-effective amount of a compound of the formula

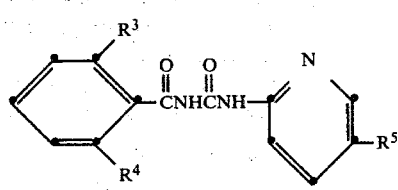

wherein $R^3$ and $R^4$ independently represent chloro or fluoro; $R^5$ is chloro, bromo or trifluoromethyl; provided that, when $R^3$ and $R^4$ are both chloro, $R^5$ is trifluoromethyl; or an acid addition salt thereof.

Compositions adapted to carrying out the method are also provided.

DESCRIPTION OF THE PREFERRED EMBODIMENTS

The above description clearly describes the novel compounds of this invention, as well as the other compounds which are also used in the method of this invention. To assure that the reader fully understands the compounds, however, the following novel compounds of this invention are mentioned: (1) 1-(2,6-difluorobenzoyl)-3-(5-trifluoromethyl-2-pyridinyl)-urea; (2) 1-(2-chloro-6-fluorobenzoyl)-3-(5-trifluoromethyl-2-pyridinyl)urea; (3) 1-(2-chloro-6-fluorobenzoyl)-3-(5-chloro-2-pyridinyl)urea; (4) 1-(2-chloro-6-fluorobenzoyl)-3-(5-bromo-2-pyridinyl)urea.

The novel compounds just mentioned are effective in the insecticidal method of this invention against manure-breeding insects. The following compounds are also effective in the new insecticidal method disclosed here: (1) 1-(2,6-dichlorobenzoyl)-3-(5-trifluoromethyl-2-pyridinyl)urea; (2) 1-(2,6-difluorobenzoyl)-3-(5-chloro-2-pyridinyl)urea; (3) 1-(2,6-difluorobenzoyl)-3-(5-bromo-2-pyridinyl)urea.

The compounds of this invention are preferably prepared by the reaction of a 2,6-dihalobenzoyl isocyanate of the formula

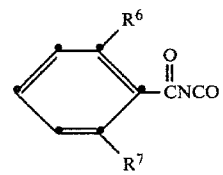

wherein $R^6$ is R or $R^3$, as the case may be, and $R^7$ is $R^1$ or $R^4$, with a 2-aminopyridine of the formula

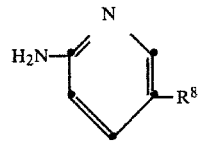

wherein $R^8$ is $R^2$ or $R^5$.

The reaction is preferably carried out in an organic solvent, such as a ketone, such as methyl ethyl ketone, methyl isobutyl ketone or acetone, a halogenated solvent such as dichloroethane, dichloromethane, chlorobenzene, 1,1,2-trichloroethane and the like, an ester such as ethyl acetate, butyl acetate, methyl propionate and the like, an aromatic such as benzene, toluene or a xylene, a nitrile such as acetonitrile, an aliphatic such as pentane, hexane or octane, or an ether such as diethyl ether, diisopropyl ether or tetrahydrofuran. The reaction is carried out at moderate temperatures, preferably at a temperature between about 0° C. and about 50° C.

The acid addition salts of the compounds of this invention are prepared in the usual manner by reacting the compound with the desired acid, in aqueous or aqueous-organic media. Acids having a low pKa of 3 or below are preferred. Acids which may be used to form the acid addition salts include hydrochloric acid, hydrobromic acid, sulfuric acid, phosphoric acid, methanesulfonic acid, hydriodic acid, toluenesulfonic acid and the like.

The 2,6-dihalobenzoyl isocyanates to be employed as starting materials are readily prepared from the corresponding 2,6-dihalobenzamides, which are commercially available, by the method of Speziale et al., *J. Org. Chem.* 27, 3742 (1962); and Wellinga et al., *J. Agric. Food Chem.* 21, 348 and 993 (1973). In this method, the benzamide is reacted with oxalyl chloride. An improved method of carrying out the reaction comprises reacting the benzamide with the oxalyl chloride in toluene at about 55° C. while water is carefully excluded, and then heating the reaction mixture to the reflux temperature after about 18 hours at the lower temperature. After about 2 hours at reflux, the reaction mixture is put under vacuum and the product is isolated by distillation.

The 5-bromo- and 5-chloro-2-aminopyridine starting materials are commercially available. The 5-trifluoromethyl-2-aminopyridine is prepared by the method of U.S. Pat. No. 3,681,369.

The compounds of this invention are also made by reacting a 2,6-dihalobenzamide of the formula

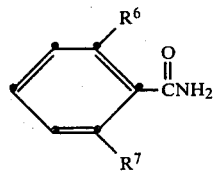

with a 2-pyridyl isocyanate of the formula

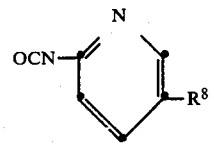

The reaction described above is preferably run at a temperature from about 50° C. to about 150° C. in an inert organic solvent such as described above, except that the higher-boiling solvents should be chosen.

The compounds of this invention may further be prepared by reacting a reactive derivative of a 2,6-dihalobenzamidocarboxylic acid of the formula

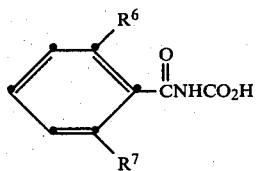

with an aminopyridine of the formula

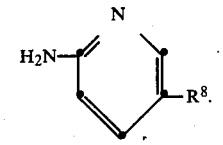

The acid just mentioned above may be used in the form of an acid chloride or bromide, or an ester. Typical esters for this purpose include the lower alkyl esters, such as methyl, ethyl, propyl and butyl esters, phenyl esters, and the more active esters such as those formed with agents typified by dicyclohexylcarbodiimide, isobutyl chloroformate, 2-ethoxy-N-ethoxycarbonyl-1,2-dihydroquinoline, methyl chloroformate, ethyl chloroformate, hydroxypentachlorobenzene, N,N-diisopropylcarbodiimide, N-cyclohexyl-N'-(2-morpholinoethyl)carbodiimide and other related reagents which are now well known in the literature.

When the acid is in the form of an acid halide, the reaction mixture should contain a hydrohalide acceptor to improve the efficiency of the reaction. Simple bases such as tertiary amines and alkali metal hydroxides, carbonates and bicarbonates may be used as the hydrohalide acceptor.

Reactions of benzamido acid derivatives with aminopyridines are carried out in inert organic solvents at temperatures in the range from about $-20°$ C. to about 100° C., of which temperatures from about 0° C. to the ambient temperature are preferred. The solvent may be any of a number of inert organic solvents, including halogenated hydrocarbons such as have been described above, or ketones or ethers as described above.

Another process for preparing the new compounds is the reaction of a benzamide of the formula

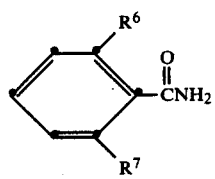

with an active derivative of a pyridinylaminocarboxylic acid of the formula

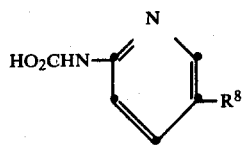

where the active derivatives are as described above.

The above reaction is best carried out at temperatures from about 50° C. to about 150° C., in inert organic solvents as described above.

All of the synthetic reactions described above consume their reactants in equimolar amounts, and so it is unnecessary to supply excess amounts of either reactant, unless it is desired, in a particular instance, to use an excess of a relatively inexpensive reactant to assure that the more costly reactant is completely used.

The following preparative examples illustrate the synthesis of compounds of this invention.

EXAMPLE 1

1-(2,6-DIFLUOROBENZOYL)-3-(5-TRIFLUOROMETHYL-2-PYRIDINYL)UREA

An 0.7 g. portion of 5-trifluoromethyl-2-aminopyridine was dissolved in 20 ml. of acetonitrile, and to the solution was added 0.85 g. of 2,6-difluorobenzoyl isocyanate under a nitrogen blanket at ambient temperature. A precipitate formed immediately. The mixture was stirred for 3 hours, and was then filtered and the solids were washed with acetonitrile. The solids were dried under vacuum to obtain 1.0 g. of the product named above, m.p. 215°–220° C. Elemental analysis gave the following results:

Calculated: C, 48.71; H, 2.34; N, 12.17. Found: C, 48.90; H, 2.39; N, 12.37.

EXAMPLE 2

1-(2-CHLORO-6-FLUOROBENZOYL)-3-(5-BROMO-2-PYRIDINYL)UREA

An 0.4 g. portion of 5-bromo-2-aminopyridine was dissolved in 20 ml. of acetonitrile, and was reacted with 0.5 g. of 2-chloro-6-fluorobenzoyl isocyanate as described in Example 1. The yield was 0.5 g. of the desired product, m.p. 207°–213° C. Elemental analysis gave the following results:

Calculated: C, 41.91; H, 2.16; N, 11.28. Found: C, 41.76; H, 1.90; N, 11.12.

EXAMPLE 3

1-(2-CHLORO-6-FLUOROBENZOYL)-3-(5-CHLORO-2-PYRIDINYL)UREA

An 0.4 g. portion of 5-chloro-2-aminopyridine was dissolved in 20 ml. of acetonitrile and reacted with 0.7 g. of 2-chloro-6-fluorobenzoyl isocyanate as described in Example 1. The yield was 0.65 g. of the product named above, m.p. 210°–215° C. Elemental analysis gave the following results:

Calculated: C, 47.59; H, 2.46; N, 12.81. Found: C, 47.34; H, 2,59; N, 12.66.

EXAMPLE 4

1-(2-CHLORO-6-FLUOROBENZOYL)-3-(5-TRIFLUOROMETHYL-2-PYRIDINYL)UREA

A portion of 5-trifluoromethyl-2-aminopyridine is reacted with 2-chloro-6-fluorobenzoyl isocyanate as described in Example 1. The reaction mixture is evaporated under vacuum and the product is recrystallized to obtain the product named above.

EXAMPLE 5

1-(2,6-DICHLOROBENZOYL)-3-(5-TRIFLUOROMETHYL-2-PYRIDINYL)UREA

A 1.1 g. portion of 2,6-dichlorobenzoyl isocyanate and 0.8 g. of 5-trifluoromethyl-2-aminopyridine were mixed in 50 ml. of ethyl acetate at ambient temperature and stirred for 18 hours. The solvent was then evaporated and the product was recrystallized from ethanol to obtain 0.2 g. of the product named above, m.p. 228°–230° C. Elemental analysis showed:

Calculated: C, 44.47; H, 2.13; N, 11.11. Found: C, 44.42; H, 2.19; N, 11.18.

EXAMPLE 6

1-(2,6-DIFLUOROBENZOYL)-3-(5-BROMO-2-PYRIDINYL)UREA

A 2 g. portion of 5-bromo-2-aminopyridine was reacted with 2.5 g. of 2,6-difluorobenzoyl isocyanate under nitrogen in 50 ml. of ethyl acetate. The reaction mixture was stirred for 3 days, and was then filtered. The solids were washed with dichloromethane, ethyl acetate and diethyl ether and dried under vacuum to obtain the desired product, m.p. 232°–235° C. The elemental analysis showed:

Calculated: C, 43.84; H, 2.26; N, 11.80. Found: C, 43.55; H, 2.24; N, 11.52.

EXAMPLE 7

1-(2,6-DIFLUOROBENZOYL)-3-(5-CHLORO-2-PYRIDINYL)UREA

An 0.5 g. portion of 5-chloro-2-aminopyridine was reacted with 0.6 g. of 2,6-difluorobenzoyl isocyanate as described in Example 1. The isolated product was 0.8 g. of the product named in the heading above, m.p. 226°–229° C. Its elemental analysis showed the following results:

Calculated: C, 50.10; H, 2.59; N, 13.48. Found: C, 49.88; H, 2.51; N, 13.21.

EXAMPLE 8

1-(2,6-DIFLUOROBENZOYL)-3-(5-TRIFLUOROMETHYL-2-PYRIDINYL)UREA

A portion of 5-trifluoromethyl-2-pyridinyl isocyanate is reacted with a portion of 2,6-difluorobenzamide in an inert organic solvent, and the reaction mixture is evaporated under vacuum and the residue is recrystallized to obtain the compound named in the heading, identical to the product of Example 1.

EXAMPLE 9

1-(2-CHLORO-6-FLUOROBENZOYL)-3-(5-BROMO-2-PYRIDINYL)UREA

A portion of 5-bromo-2-pyridinyl isocyanate is dissolved in an inert organic solvent and is reacted with 2-chloro-6-fluorobenzamide as described in Example 8. The product is isolated as described in that example to obtain a portion of the product named in the heading, identical to the product of Example 2.

EXAMPLE 10

1-(2-CHLORO-6-FLUOROBENZOYL)-3-(5-CHLORO-2-PYRIDINYL)UREA

A portion of 2-chloro-6-fluorobenzamide is reacted with 5-chloro-2-pyridinyl isocyanate as described in Example 8, and the product is isolated and purified as described in that example to obtain a significant yield of the product named in the heading, identical to the product of Example 3.

EXAMPLE 11

1-(2-CHLORO-6-FLUOROBENZOYL)-3-(5-TRIFLUOROMETHYL-2-PYRIDINYL)UREA

A portion of 2-chloro-6-fluorobenzamide is reacted with 5-trifluoromethyl-2-pyridinyl isocyanate as described in Example 8, and the product is isolated as described in that example to obtain the compound named above, identical to the product of Example 4.

EXAMPLE 12

1-(2,6-DIFLUOROBENZOYL)-3-(5-TRIFLUOROMETHYL-2-PYRIDINYL)UREA

A portion of 5-trifluoromethyl-2-aminopyridine is reacted with 2,6-difluorobenzamidocarboxylic acid chloride in an inert organic solvent in the presence of a hydrogen halide acceptor. The reaction mixture is washed with water and neutralized, and the organic layer is evaporated to dryness to obtain the product named in the heading, identical to the product of Example 1.

EXAMPLE 13

1-(2-CHLORO-6-FLUOROBENZOYL)-3-(5-BROMO-2-PYRIDINYL)UREA

To a portion of 2-chloro-6-fluorobenzamidocarboxylic acid chloride dissolved in an organic solvent, a hydrogen halide acceptor is added, and a portion of 5-bromo-2-aminopyridine is added. After a period of stirring, the reaction mixture is washed with water and neutralized, and the product named in the heading is isolated as described in Example 12. The product is identical to that of Example 2 above.

EXAMPLE 14

1-(2-CHLORO-6-FLUOROBENZOYL)-3-(5-CHLORO-2-PYRIDINYL)UREA

A portion of 5-chloro-2-aminopyridine is reacted with 2-chloro-6-fluorobenzamidocarboxylic acid chloride in the presence of a hydrogen halide acceptor as described in Example 12. The product, named in the heading above, is isolated as described in Example 12 to obtain the desired compound, identical to the product of Example 3.

EXAMPLE 15

1-(2-CHLORO-6-FLUOROBENZOYL)-3-(5-TRIFLUOROMETHYL-2-PYRIDINYL)UREA

A portion of 2-chloro-6-fluorobenzamidocarboxylic acid chloride is reacted with 5-trifluoromethyl-2-aminopyridine in an organic solvent in the presence of a hydrogen halide acceptor as described in the examples above. The product is isolated as described in Example 12 above to obtain the compound named in the heading, identical to the product of Example 4.

EXAMPLE 16

1-(2,6-DIFLUOROBENZOYL)-3-(5-TRIFLUOROMETHYL-2-PYRIDINYL)UREA

To a portion of 2,6-difluorobenzamide dissolved in an inert organic solvent is added a portion of 5-trifluoromethyl-2-pyridinylaminocarboxylic acid, phenyl ester, and the reaction mixture is stirred at elevated temperature. After a period of stirring, the mixture is evaporated under vacuum, and the product is recrystallized to obtain the product named in the heading, identical to the product of Example 1.

EXAMPLE 17

1-(2-CHLORO-6-FLUOROBENZOYL)-3-(5-BROMO-2-PYRIDINYL)UREA

A portion of 2-chloro-6-fluorobenzamide is dissolved in an organic solvent, and 5-bromo-2-pyridinylaminocarboxylic acid, phenyl ester is added. The reaction mixture is stirred with heating for a period of time, and is then evaporated under vacuum. The product, identical to the product of Example 2 above, is isolated from the residue by recrystallization.

EXAMPLE 18

1-(2-CHLORO-6-FLUOROBENZOYL)-3-(5-CHLORO-2-PYRIDINYL)UREA

A portion of 5-chloro-2-pyridinylaminocarboxylic acid, phenyl ester, is reacted with 2-chloro-6-fluorobenzamide as described in Example 16. The product named in the heading above, identical to the product of Example 3, is isolated by evaporating the reaction mixture, and recrystallizing the product from the residue.

EXAMPLE 19

1-(2-CHLORO-6-FLUOROBENZOYL)-3-(5-TRIFLUOROMETHYL-2-PYRIDINYL)UREA

A portion of 2-chloro-6-fluorobenzamide is reacted with 5-trifluoromethyl-2-pyridinylaminocarboxylic acid, phenyl ester, in an inert organic solvent at elevated temperature to product the product named in the heading above, identical to the product of Example 4, which is isolated by evaporating the reaction mixture and recrystallizing the product.

EXAMPLE 20

1-(2,6-DIFLUOROBENZOYL)-3-(5-TRIFLUOROMETHYL-2-PYRIDINYL)UREA

A portion of 5-trifluoromethyl-2-aminopyridine is dissolved in an inert organic solvent, and to the solution is added a portion of 2,6-difluorobenzamidocarboxylic acid, 4-nitrophenyl ester. The reaction mixture is stirred at elevated temperature for a period of time, after which the reaction mixture is evaporated to dryness under vacuum, and the product named in the heading above, identical to the product of Example 1, is isolated by recrystallization.

EXAMPLE 21

1-(2-CHLORO-6-FLUOROBENZOYL)-3-(5-BROMO-2-PYRIDINYL)UREA

To a solution of 2-chloro-6-fluorobenzamidocarboxylic acid, 4-nitrophenyl ester, in an inert organic solvent is added 5-bromo-2-aminopyridine. The reaction mixture is stirred at an elevated temperature for a period of time, and is then evaporated to dryness under vacuum. The product named in the heading above, identical to the product of Example 2, is isolated and purified by recrystallization.

EXAMPLE 22

1-(2-CHLORO-6-FLUOROBENZOYL)-3-(5-CHLORO-2-PYRIDINYL)UREA

A portion of 2-chloro-6-fluorobenzamidocarboxylic acid, 4-nitrophenyl ester, is combined with a portion of 5-chloro-2-aminopyridine in an inert organic solvent. The reaction mixture is stirred at elevated temperature for a period of time, and is then evaporated under vacuum. The product named in the heading above, identical to the product of Example 3, is isolated by recrystallization.

EXAMPLE 23

1-(2-CHLORO-6-FLUOROBENZOYL)-3-(5-TRIFLUOROMETHYL-2-PYRIDINYL)UREA

A solution is made in an inert organic solvent of 2-chloro-6-fluorobenzamidocarboxylic acid, 4-nitrophenyl ester, and 5-trifluoromethyl-2-aminopyridine. The temperature of the reaction mixture is raised, and the mixture is stirred for a period of time. The mixture is then evaporated under vacuum, and the product named in the heading above, identical to the product of Example 4, is isolated and purified by recrystallization.

The activity of the compounds discussed in this document will be explained below. The novel compounds of this invention are generally useful as insecticides, and their utility as such will first be described. The novel method of this invention for controlling manure-breeding insects will then be described, which description will include the use of both the novel compounds of this invention and the use of the other compounds which have been discussed above.

The novel compounds of the present invention are useful for the control of insects of various orders, including Coleoptera such as Mexican bean beetle, boll weevil, corn rootworms, cereal leaf beetle, flea beetles, borers, Colorado potato beetle, grain beetles, alfalfa weevil, carpet beetle, confused flour beetle, powder post beetle, wireworms, rice weevil, rose beetle, plum curculio, and white grubs; Diptera, such as house fly, yellow fever mosquito, stable fly, horn fly, blowfly, cabbage maggot, and carrot rust fly; Lepidoptera, such as southern armyworm, codling moth, cutworm, clothes moth, Indian meal moth, leaf rollers, corn earworm, European corn borer, cabbage worm, cabbage looper, cotton bollworm, bagworm, eastern tent caterpillar, sod webworm, and fall armyworm; and Orthoptera, such as German cockroach and American cockroach.

It is believed that the present compounds act by interfering with the mechanism of metamorphosis which occurs in insects, causing the death of the insects. It is also believed that ingestion by the insects is necessary to invoke this mechanism. While the death of any given insect may be delayed until that insect reaches some stage of metamorphosis, the net result of this activity is the control and suppression of insects.

Therefore, in another embodiment, the present invention is directed to a method of suppressing insects which comprises applying to a locus of the insects an effective amount of a novel compound of the present invention. The locus can be of any environment inhabited by insects to be controlled, such as soil, air, water, foods, vegetation, manure, inert objects, stored matter such as grain, and the like.

Preferably the compounds of the present invention are supplied in a formulation, for ease of application. The compounds can be formulated with various adjuvants, including water, organic liquids, surface-active agents, inert solids, and the like. Suitable surface-active agents include anionic agents, such as sodium lauryl sulfate, sodium dodecylbenzenesulfonate, and the like; and nonionic agents, such as polyethylene glycol p-nonylphenol ether. Mixtures are often desirably employed. The formulation can take the form of a liquid, dust, granule or aerosol, etc. The formulation can be concentrated, as in a slow-release formulation or as in a formulation to be diluted with water before application to the locus of insects. Many methods of formulation are known in the art and can be employed in implementing the present invention.

The concentration of active agent in the formulation is not critical, inasmuch as an effective concentration will vary with the nature of the locus to be treated, the severity of insect infestation, the susceptibility of the particular insects involved, etc. In general, concentrations ranging from about 0.1 to 1,000 ppm. give good results. As exemplified below, lesser concentrations of from about 5 to about 100 ppm. have given good control of southern armyworm.

The insecticidal activity of the compounds of this invention was determined by a number of tests. In one test, the compounds were tested against Mexican bean beetle larvae (*Epilachna varivestis*), and against southern armyworm larvae (*Spodoptera eridania*). These insects are members of the Coleoptera and Lepidoptera orders of insects, respectively. The formulations were applied to the foliage of plants and the larvae were subsequently permitted to feed on the foliage. The compounds were tested in a number of concentrations described in the tables below.

Each compound to be tested was formulated by dissolving 10 mg. of the compound in 1 ml. of a solvent made up with 23 g. of Toximol R and 13 g. of Toximol S per liter of 1:1 anhydrous ethanol:acetone. Each of Toximol R and Toximol S is a sulfonate/nonionic blend produced by Stepan Chemical Co., Northfield, Ill., U.S.A. Water was then added to obtain 10 ml. of solution containing the compound in a concentration of 1,000 ppm. Alternatively, 11 mg. of compound was used, to make up 11 ml. of solution, of which 10 ml. was employed as a 1000 ppm. treating solution, and of which the remaining 1 ml. was diluted further with water to obtain a treating solution containing 100 ppm. of compound. Formulations of the compound at lesser concentrations were prepared in the same manner, using the same solvent.

Each solution of test compound was sprayed onto two 4-inch square pots of bean plants containing 6 to 10 plants per pot. The plants were allowed to dry and then 12 leaves were removed and the cut ends wrapped in water-soaked cellucotton. The leaves were divided between six 100×20 mm. plastic petri dishes. Five second-instar Mexican bean beetle larvae and 5 second- and third-instar southern armyworm larvae were placed in each of 3 dishes. The dishes were then placed in a room wherein the temperature and relative humidity were controlled at about 25° C. and about 51% for a period of 4 days, at which time the first evaluation of the effects of the test compounds was made. After this evaluation, 2 fresh leaves from the original treated pots were placed in each dish. The dishes were again maintained in the temperature and humidity controlled room for an additional 3 days until the final 7-day evaluation was made.

Insecticidal effect was determined by counting the number of living larvae of each species and applying the following rating code:
0=All larvae living
1=Half or more than half of the larvae living
2=Less than half of the larvae living
3=All larvae dead The results of this test are set forth in Table 1, which follows. In the table, column 1 identifies the compound by the number of its preparative example; column 2 lists the concentration of the test compound in the formulation; and columns 3 thru 6 gives the rating code at days 4 and 7 for the two insects against which the compounds were tested.

TABLE 1

| Example | Appln. Rate PPM. | Mexican bean beetle | | Southern armyworm | |
|---|---|---|---|---|---|
| | | 4 days | 7 days | 4 days | 7 days |
| 1 | 1000 | 3 | 3 | 3 | 3 |
| 1 | 100 | 3 | 3 | 2 | 2 |
| 2 | 1000 | — | — | 3 | 3 |
| 2 | 100 | 1 | 3 | 3 | 3 |
| 2 | 10 | 1 | 2 | 3 | 3 |
| 3 | 1000 | — | — | 3 | 3 |
| 3 | 100 | 1 | 3 | 3 | 3 |
| 3 | 10 | 1 | 3 | 3 | 3 |

In a further evaluation, the compounds of the present invention were retested in the same procedure described above but at lower concentrations, against southern armyworm only. In the retest, percent control was determined by counting the number of living larvae per dish and using Abbott's formula [W. W. Abbott, "A Method of Computing the Effectiveness of an Insecticide," J. Econ. Entomol. 18, 265–67 (1925)]:

Percent Control =

-continued $$\frac{\text{No. of survivors in control} - \text{No. of survivors in treatment} \times 100}{\text{No. survivors in control}}$$

The results are set forth in Table 2 which follows.

TABLE 2

| Example | Appln. Rate PPM. | Percent Control | |
|---|---|---|---|
| | | 4 days | 7 days |
| 1 | 100 | 0 | 100 |
| 1 | 50 | 0 | 100 |
| 1 | 25 | 0 | 27 |
| 1 | 10 | 0 | 20 |
| 1 | 100 | 60 | 67 |
| 1 | 50 | 0 | 20 |
| 1 | 25 | 7 | 13 |
| 1 | 10 | 0 | 0 |
| 2 | 100 | 100 | 100 |
| 2 | 50 | 100 | 100 |
| 2 | 25 | 100 | 100 |
| 2 | 10 | 100 | 100 |
| 2 | 10 | 100 | 100 |
| 2 | 5 | 100 | 100 |
| 2 | 2.5 | 100 | 100 |
| 2 | 1 | 27 | 80 |
| 2 | 1 | 20 | 40 |
| 2 | .5 | 0 | 0 |
| 2 | .25 | 0 | 0 |
| 2 | .125 | 0 | 0 |
| 3 | 100 | 100 | 100 |
| 3 | 50 | 100 | 100 |
| 3 | 25 | 100 | 100 |
| 3 | 10 | 100 | 100 |
| 3 | 10 | 100 | 100 |
| 3 | 5 | 100 | 100 |
| 3 | 2.5 | 100 | 100 |
| 3 | 1 | 40 | 60 |

The compounds have been evaluated in a test against the common house fly, Musca domestica. The test was carried out as follows.

Three mg. of each test compound was dissolved in 3 ml. of the same ethanol:acetone solution described above, and the solution was made up to 30 ml. with water. Five ml. of the aqueous solution was thoroughly mixed in a quart jar with 250 g. of an artificial diet, composed of Chemical Specialties Manufacturers Association house fly medium with added yeast and malt.

A concentration of 2 ppm. by weight in the diet was thus provided. Lower concentrations, as set out in Table 3 below, were provided by using further dilutions of the test compound solution.

Twenty-five fresh house fly eggs were counted on a filter paper, and the filter paper was placed in the jar with the treated diet. The jar was covered with a paper towel, fastened with an elastic band. The jar was then stored at 25° C. and 45% relative humidity, while the house fly eggs hatched and the larvae matured and pupated.

Seven days after establishing the test, the pupae were collected and counted, and the mortality of the flies from the egg stage to the pupae stage was calculated as percent control.

The pupae were held at ambient temperature for one more week, and the number of adult flies which developed were counted. The overall percent control of the house flies, from the egg stage to the adult stage, was then calculated. Results obtained from testing compounds of this invention in the above test were as follows.

TABLE 3

| Example | Appln. Rate PPM. | Percent Control | |
|---|---|---|---|
| | | 7 days | 14 days |
| 1 | 2 | 100 | 100 |
| 1 | 1 | 88 | 100 |
| 1 | .5 | 36 | 100 |
| 1 | .2 | 0 | 92 |
| 1 | .02 | 0 | 40 |
| 1 | 1 | 100 | 100 |
| 1 | .5 | 98 | 100 |
| 1 | .2 | 92 | 100 |
| 1 | .02 | 0 | 10 |
| 1 | 2 | 64 | 91 |
| 1 | 2 | 100 | 100 |
| 1 | 1 | 100 | 100 |
| 1 | 2 | 100 | 100 |
| 1 | 1 | 100 | 100 |
| 2 | 2 | 94 | 100 |
| 2 | 1 | 50 | 86 |
| 2 | 2 | 78 | 98 |
| 2 | 1 | 34 | 96 |
| 3 | 2 | 86 | 96 |
| 3 | 1 | 78 | 94 |
| 3 | 2 | 92 | 98 |
| 3 | 1 | 58 | 88 |

The compound of Example 1 has been further evaluated in other tests against Mexican bean beetle, which were carried out substantially according to the method described above in the explanation of Table 2.

TABLE 4

| Example | Appln. Rate PPM. | Percent Control | |
|---|---|---|---|
| | | 4 days | 7 days |
| 1 | 1000 | 87 | 100 |
| 1 | 100 | 87 | 100 |
| 1 | 50 | 67 | 93 |

Another test, against the black cutworm (*Agrotis ipsilon*), was conducted, using the compound of Example 1. The test was carried out according to the same method described above in the explanations of Tables 1 and 2, except that the plant used was maize of the Golden Bantam variety.

TABLE 5

| Example | Appln. Rate PPM. | Percent Control | |
|---|---|---|---|
| | | 5 days | 7 days |
| 1 | 50 | 0 | 7 |
| 1 | 10 | 0 | 0 |
| 1 | 5 | 0 | 0 |
| 1 | 1 | 0 | 0 |

A test was conducted to determine the effect of the compound of Example 1 on adult house flies. The test was carried out by placing 100 house fly pupae in a cage, with a supply of water and an artificial diet made up of equal parts of cane sugar and non-fat dry milk, containing various concentrations of the compound. The house flies emerged from their pupae and fed on the treated diet for 4 or 5 days. An oviposition container was placed in each cage, where the adult flies laid their eggs. The container was observed and the percent hatch of the eggs was recorded.

The treated diet was removed after one week, and was replaced with untreated diet of the same type, to see if the chemosterilant effect was sustained.

The compound of Example 1 was added to the diet at 1% and 0.1% by weight. In both treatments the eggs which were laid one week after treatment started were non-viable; none of the eggs hatched.

One week after the treated diet had been removed from the cages, and replaced with normal diet, eggs freshly laid by the flies which had been fed the 1% treated diet were still completely non-viable; none hatched. Fifty percent of the eggs laid by the flies fed the 0.1% diet hatched.

Twelve days after the treated diet had been removed, 100% of the eggs laid by the flies on the original 1% diet, and 62.5% of the eggs laid by the flies on the original 0.1% diet, failed to hatch.

Nineteen days after the treated diet had been removed, 97.5% of the eggs laid by the flies on the original 1% diet, and 67.5% of the eggs laid by the flies on the original 0.1% diet, failed to hatch.

A test was done to determine the ovicidal activity of compounds of this invention against the eggs of typical insects. In this test, Mexican bean beetle and southern armyworm adults were allowed to deposit their eggs on the leaves of bean plants, and the eggs were treated by dipping leaves of the plants into solutions of the test compound, which solutions had been prepared as described above in the explanatory matter introducing Tables 1 and 2. The concentration of the test compound in the solutions was 50 ppm. by weight, and the test compound was that of Example 1. The results of the experiment showed 100% ovicidal effect against the eggs of both Mexican bean beetles and southern armyworms. None of the treated eggs hatched.

A test has been conducted against the blowfly, *Phormia regina*, at a concentration of 10 ppm. by weight. The test was conducted by preparing a 100 ppm. solution of the test compound in 10% aqueous dimethylformamide, and mixing 0.2 ml. of the solution with 1.8 ml. of bovine serum. The treated serum was absorbed on a dental wick in a test tube, and 50 first-instar blowfly larvae were placed on the wick. The test tube was covered with a ball of cotton and incubated at 27° C. for 24 hours.

The live larvae were then counted, and it was found that the compound of Example 1 killed 45 of the 50 larvae exposed to it.

A test has been conducted against the beet armyworm, *Spodoptera exigna*. The test method was the same as that explained above in the introductory matter to data Table 2. Again, the plant to which the compounds were applied was the bean plant, and various compound concentrations were used as recited below.

TABLE 6

| Example | Appln. Rate PPM. | Percent Control 4 days |
|---|---|---|
| 2 | 50 | 13* |
| 2 | 10 | 7* |
| 2 | 1 | 0* |
| 3 | 50 | 93 |
| 3 | 10 | 100 |
| 3 | 1 | 60 |

The same type of test has also been conducted against corn earworm, *Heliothis zea*. In this test, the insects were exposed to the leaves of treated corn plants, but in other respects the test was as described above in the introductory matter to Table 2. The compound of Example 2 was tested at 50, 10 and 1 ppm., and it was found that all rates were inactive when observed after 4 days. When observed after 7 days, the highest rate was found to kill 20% of the earworms, and the lower 2 rates were inactive.

The use of insecticides by oral administration to animals for the control of manure-breeding insects is a rather new concept in insect control. At the present time, only a few insecticides are so used, of which a standard reference compound is diflubenzuron, 1-(2,6-difluorobenzoyl)-3-(4-chlorophenyl)urea.

The compounds are active against the larvae of insects which breed in manure, especially insects of the order Diptera. Especially important manure-breeding insects, against which the method of this invention is particularly effective, include the house fly (*Musca domestica*), the stable fly (*Stomoxys calcitrans*), the horn fly (*Haematobia irritans*), and the face fly (*Musca autumnalis*).

The compounds used in the method of this invention are orally administered to the animals to be treated, and pass essentially unchanged through the alimentary tract of the animal. The compound thus is excreted in the animal's feces, where it is effective against the larvae of insects. The animals which may be treated in accordance with the present method include especially poultry, such as chickens, ducks, turkeys and geese; ruminants, such as cattle, sheep and goats; and economic monogastric animals, such as horses and swine. The compounds may also be used, if desired, in carnivorous animals, such as those of the cat and dog families.

Use of the method of this invention in poultry, especially chickens, and in ruminants, especially bovines, is most highly preferred.

The exact means by which the compounds used in the method of this invention are administered to the animals is not critical. It is easiest and most convenient, of course, to mix the compound in the animal's feed. When the compounds are administered as feed additives, they may be used in concentrations in the feed ranging from about 1 ppm. to about 50 ppm. by weight. A preferred range of concentration is from about 1 ppm. to about 10 ppm. by weight.

The formulation of feed additives into animal feeds is a well known art. It is usual to make a concentrated premix as a raw material for treated feeds. The formulation of the premix is guided solely by convenience in mixing feed from the premix, and by economy. The premix may contain from about 1 to about 400 g./lb. of the insecticide, depending on convenience in mixing feed containing the desired concentration of the compound. Premixes may be either liquid or solid.

The improved feed premixes which are provided by this invention, which are novel because of the presence of the insecticides used in the method of this invention, are formulated in any of the conventionally-used physiologically-acceptable carriers. Liquid carriers which are suitable for premix use include glycols such as polyethylene glycols of various molecular weights and propylene glycol, inert oils including vegetable oils and highly-refined mineral oil, and physiologically-acceptable alcohols such as ethanol. Solid premix carriers include vermiculite, diatomaceous earth, physiologically-acceptable clays such as attapulgite and montmorillonite, and granulated or powdered feed components such as cracked corn, soybean meal, alfalfa meal, rice hulls, corn cobs, cracked wheat or oats, and waste materials of grain processing.

It will further be understood by those skilled in animal husbandry that animal feeds containing from about 1 ppm. to about 50 ppm. by weight of a compound useful in the method of this invention are novel and are important embodiments of the invention. Such feeds may preferably be in the form of cereal-based feeds, adapted to the needs of poultry, ruminants and/or monogastric animals such as horses and swine. The usual dry or slurried animal feeds, based on grains such as wheat, oats, barley, maize and the like, may be treated with compounds used in the method of this invention, just as animal feeds are routinely treated with medicaments and parasiticides in the ordinary practice of the animal husbandry art.

The compounds may also be administered as additives to the animal's drinking water, in which case they should be used in a concentration of from about 1 ppm. to about 30 ppm., preferably from about 1 ppm. to about 15 ppm.

Administration of the compounds by means of sustained release boluses is particularly advantageous when ruminants, especially cattle, are to be treated. Such boluses are made as tablets are made, except that a means to delay the dissolution of the compound over a period of time is provided. Boluses may be made to release the compound steadily over long periods of time, even 100 days or more. A number of polymeric substances have been used to prepare slow-release boluses; particularly effective polymers are the copolymers of polylactic and polyglycolic acids. It is necessary to retain a slow-release bolus in the rumen of the treated ruminant, so that the bolus is not carried on out of the digestive tract. Boluses are retained in the rumen most easily by making them of a high-density material, as by mixing metal particles into the composition, or by providing wings which open in the rumen and make the bolus too large to get through the opening into the omasum of the animal. Boluses should release from about 0.01 mg./kg. of body weight/day to about 2 mg./kg./day, preferably from about 0.01 to about 0.25 mg./kg./day.

The compounds may also be administered, of course, in the form of pharmaceutical dosage forms, such as tablets, capsules, drenches, suspensions and the like, but administration in such forms is usually not preferred because of the relative inconvenience of such administration.

Mineral blocks provide another advantageous formulation with which to administer the insecticides, particularly to ruminant animals. Such blocks are usually supplied to ruminants, even to those on pasture. The usual blocks are highly compressed forms of physiologically-desirable salts and nutritive substances, generally including phosphates, carbonates, halides, calcium salts, trace elements such as zinc, cobalt, manganese and the like, vitamins, steroids, and lubricants and binders to assist in compression.

Mineral blocks are, of course, old in the animal husbandry art. The addition of the insecticides of the present method, however, provides novel blocks which are important embodiments of the present invention. The insecticides should be added to the blocks in concentrations from about 0.01% to about 0.5%, preferably from about 0.05% to about 0.25%.

It is necessary, of course, to administer at least an insecticidally-effective amount of compound to the animal to be treated. It is most effective to measure the amount administered, however, as a concentration in the medium with which it is combined. Effective insecticidal amounts, or concentrations, are described above.

It is not implied, of course, that administration of any amount of any compound used in the method of this invention will kill all larvae of all manure-breeding insects. It is not in the nature of biological methods to be invariably 100% effective. However, the oral administration of a compound of the present method, in an insecticidally-effective amount, will produce a worthwhile reduction in the number of insect larvae which mature in the manure of the treated animal. In many cases, of course, complete control of the larvae will result, and no adults will develop. It will be understood that partial control of the manure-breeding insects is significant and beneficial, and that the population of the insects is usefully reduced, even though not all of them may be killed by the insecticidal treatment.

Control of manure-breeding insects in accordance with the present invention is, clearly, more convenient and effective than is insect control by traditional methods of applying insecticides to the manure after it has been gathered and piled. The added operation of spraying or dusting insecticides over the manure is avoided. More importantly, the method of this invention results in the insecticidal compounds being intimately mixed through the mass of the manure, so that any larvae in the mass are sure to come into contact with the compound.

The ability of the method of this invention to suppress manure-breeding insects has been evaluated with the following test procedure. A group of chickens averaging 1.6–1.8 kg. were used. The chickens were placed in wire cage pens, 2 birds per pen, and each pen was used as a treatment group. Each pen was equipped with an automatic watering trough and a feed container, and water and feed were continuously available to the birds.

Treated chicken feeds were made up, containing various concentrations of the test compound, as shown in the table below. The treated feed was fed for 6 weeks, and then the birds were given untreated feed for 6 weeks more.

A sample of approximately 0.5 kg. of droppings was collected from each pen once a week, and the larvicidal effect was determined by moistening each sample with water, and seeding 100 housefly eggs to each of the samples. The seeded samples, in 1-liter plastic containers, were covered with muslin and held at room temperature until evaluated. The effect of the treatments was determined by counting the live pupae in the samples, and expressing the number of pupae in terms of percent control of the pupae, compared to the untreated control samples.

In the first test to be reported here, each concentration level of the compound was administered to 2 pens of birds. The percent control was determined on a number of samples obtained at a number of times during the experiment, as described in the table below; it should be kept in mind that the administration of treated feed ended after the sixth week of the experiment, and that the birds were fed untreated feed thereafter.

TABLE 7

| Example | Conc., ppm. | Percent Control at Treatment Week | | | | | | | | |
|---|---|---|---|---|---|---|---|---|---|---|
| | | 0 | +1 | 2 | 3 | 4 | 5* | 6 | 7 | 8 |
| 7 | 3.8 | 1.1 | 35 | 66 | 40 | 98 | 94 | 80 | 15 | 15 |
| 7 | 7.5 | 0 | 100 | 100 | 99 | 97 | 99 | 100 | 12 | 10 |
| 7 | 15 | 6.9 | 100 | 100 | 100 | 100 | 100 | 99 | 28 | 19 |
| 7 | 30 | 0.5 | 100 | 100 | 100 | 100 | 100 | 93 | 51 | 13 |
| Blank | | 0 | 0 | 0 | 0 | 0 | 0 | 0 | 0 | 0 |

+Start of treatment period
*End of treatment period

The data above shows that the method of this invention is not only effective to suppress manure-breeding insects, but that it continues to be effective for at least a week after the administration of the compound is stopped.

The birds used in the above experiment gained weight normally, and showed no ill effects due to the administration of the compound.

Another test was carried out, according to the method of the experiment described above, except that data was obtained at only one time, 7 days after the administration of the compound started. The compound of Example 1 was administered at 3.8, 7.5, 15 and 30 ppm. by weight in the feed, and all treatments were 100% effective. No house flies seeded on the manure of the test birds were able to mature.

I claim:

1. A feed premix for the control of manure-breeding insects comprising an edible physiologically-acceptable feed premix carrier and from about 1 to about 400 g./lb. of a compound of the formula

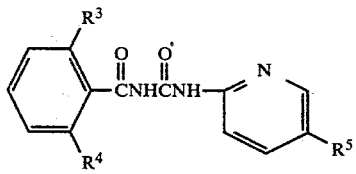

wherein
$R^3$ and $R^4$ independently represent chloro or fluoro;
$R^5$ is chloro, bromo or trifluoromethyl; provided that, when $R^3$ and $R^4$ are both chloro, $R^5$ is trifluoromethyl; or a physiologically-acceptable acid addition salt thereof.

2. A feed premix of claim 1 wherein the compound is 1-(2,6-difluorobenzoyl)-3-(5-trifluoromethyl-2-pyridinyl)urea.

3. A feed premix of claim 1 wherein the compound is 1-(2,6-difluorobenzoyl)-3-(5-chloro-2-pyridinyl)urea.

4. A sustained release bolus for the control of manure-breeding insects comprising a polymeric substance and a compound of the formula

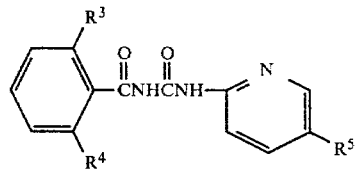

wherein $R^3$ and $R^4$ independently represent chloro or fluoro; $R^5$ is chloro, bromo or trifluoromethyl; provided that, when $R^3$ and $R^4$ are both chloro, $R^5$ is trifluoromethyl; or a physiologically-acceptable acid addition salt thereof, wherein the bolus releases from about 0.01 mg./day of the compound per kg. of body weight of the animal to which the bolus is administered, to about 2 mg./kg./day.

5. A bolus of claim 4 wherein the compound is 1-(2,6-difluorobenzoyl)-3-(5-trifluoromethyl-2-pyridinyl)urea.

6. A bolus of claim 4 wherein the compound is 1-(2,6-difluorobenzoyl)-3-(5-chloro-2-pyridinyl)urea.

7. A mineral block for the control of manure-breeding insects comprising physiologically-desirable salts, nutritive substances, a physiologically-acceptable diluent, and an effective concentration of a compound of the formula

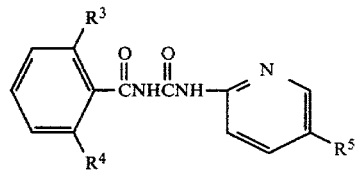

wherein $R^3$ and $R^4$ independently represent chloro or fluoro; $R^5$ is chloro, bromo or trifluoromethyl; provided that, when $R^3$ and $R^4$ are both chloro, $R^5$ is trifluoromethyl; or a physiologically-acceptable acid addition salt thereof.

8. A mineral block of claim 7 wherein the compound is 1-(2,6-difluorobenzoyl)-3-(5-trifluoromethyl-2-pyridinyl)urea.

9. A mineral block of claim 7 wherein the compound is 1-(2,6-difluorobenzoyl)-3-(5-chloro-2-pyridinyl)urea.

* * * * *

UNITED STATES PATENT AND TRADEMARK OFFICE
CERTIFICATE OF CORRECTION

PATENT NO. : 4,338,321
DATED : July 6, 1982
INVENTOR(S) : John L. Miesel

It is certified that error appears in the above—identified patent and that said Letters Patent is hereby corrected as shown below:

Column 13, line 60, under the Table, add --*Observed after only 2 days--.

Signed and Sealed this

Twenty-sixth Day of October 1982

[SEAL]

Attest:

Attesting Officer

GERALD J. MOSSINGHOFF

Commissioner of Patents and Trademarks